(12) United States Patent
Ivanjesku et al.

(10) Patent No.: US 10,959,950 B2
(45) Date of Patent: Mar. 30, 2021

(54) STABILIZED COMPOSITIONS FOR THE CONTROLLED DELIVERY OF PROBIOTICS AND METHODS OF PRODUCTION THEREOF

(71) Applicant: DAKOTA BIOTECH, LLC, Sarasota, FL (US)

(72) Inventors: MaryAnne Maya Ivanjesku, Duette, FL (US); Kristin Daugherty, Lakewood Ranch, FL (US); Tatjana Bohinc, Cary, NC (US); Stephen Buckley, New York, NY (US)

(73) Assignee: DAKOTA BIOTECH, LLC, Sarasota, FL (US)

( * ) Notice: Subject to any disclaimer, the term of this patent is extended or adjusted under 35 U.S.C. 154(b) by 16 days.

(21) Appl. No.: 16/160,044

(22) Filed: Oct. 15, 2018

(65) Prior Publication Data

US 2019/0046439 A1  Feb. 14, 2019

Related U.S. Application Data

(63) Continuation of application No. PCT/US2018/034571, filed on May 25, 2018.

(60) Provisional application No. 62/511,374, filed on May 26, 2017.

(51) Int. Cl.
| | | |
|---|---|---|
| *A61K 9/107* | (2006.01) | |
| *A61K 35/741* | (2015.01) | |
| *A61K 9/08* | (2006.01) | |
| *A61K 47/02* | (2006.01) | |
| *A61K 47/12* | (2006.01) | |
| *A61K 47/18* | (2017.01) | |
| *A61K 47/36* | (2006.01) | |
| *A61K 47/44* | (2017.01) | |
| *A61K 9/00* | (2006.01) | |
| *A61K 35/00* | (2006.01) | |

(52) U.S. Cl.
CPC .......... *A61K 9/107* (2013.01); *A61K 9/08* (2013.01); *A61K 35/741* (2013.01); *A61K 47/02* (2013.01); *A61K 47/12* (2013.01); *A61K 47/18* (2013.01); *A61K 47/36* (2013.01); *A61K 47/44* (2013.01); *A61K 9/0014* (2013.01); *A61K 2035/115* (2013.01)

(58) Field of Classification Search
None
See application file for complete search history.

(56) References Cited

FOREIGN PATENT DOCUMENTS

WO  0009088 A1  2/2000

OTHER PUBLICATIONS

Bayoumi, Mariam, et al., "Multi-compartment encapsulation of communicating droplets and droplet networks in hydrogel as a model for artificial cells", Scientific Reports, Apr. 3, 2017, pp. 1-11, vol. 7, Article 45167.

Dafe, Alireza, et al., "Investigation of Pectin/Starch Hydrogel as a Carrier for Oral Delivery of Probiotic Bacteria", International Journal of Biological Macromolecules, Jan. 17, 2017, pp. 536-543, vol. 97.

Malo De Molina, Paula, et al., "Oil-in-Water-in-Oil Multinanoemulsions for Templating Complex Nanoparticles", Nano Letters, Jul. 25, 2016, pp. 7325-7332, vol. 16.

Nesrinne, S. et al., "Synthesis, characterization and rheological behavior of pH sensitive poly(acrylamide-coacrylicacid) hydrogels", Arabian Journal of Chemistry, 2017 (Published online: Nov. 23, 2013), pp. 539-547, vol. 10.

ISA/KR, International Search Report and Written Opinion for International Patent Application No. PCT/US2018/034571, dated Sep. 19, 2018.

International Preliminary Report on Patentability for International Patent Application No. PCT/US2018/034571, dated Nov. 26, 2019, 6 Pages.

*Primary Examiner* — Melissa L Fisher
(74) *Attorney, Agent, or Firm* — NK Patent Law

(57) ABSTRACT

A stabilized composition for the controlled delivery of probiotics includes an aqueous solution of crystalloids and colloids comprised of water insoluble polymers with the ability to de-swell upon electrical charge. The composition further includes a plurality of oil droplets and a base solution. The composition further include a destabilizing solution comprising a solvent, nitrogen, a natural acid sufficient to produce a pH of about 3.0 to about 4.5, and a sufficient amount of a salt to contribute to an osmolality between about 190 mOsm/L and about 900 mOsm/L. The composition further includes a plurality of microencapsulated probiotic beads, wherein the plurality of microencapsulated probiotic beads comprises between about 0.01% to about 20% of the composition by weight.

4 Claims, 3 Drawing Sheets

STABILIZED COMPOSITIONS FOR THE CONTROLLED DELIVERY OF PROBIOTICS AND METHODS OF PRODUCTION THEREOF

CROSS-REFERENCE TO RELATED APPLICATION

This application is a continuation of International Patent Application No. PCT/US2018/034571, filed May 25, 2018, which claims the benefit of priority of U.S. Provisional Patent Application No. 62/511,374 titled "Stabilized Compositions for the Controlled Delivery of Probiotics and Methods of Production Thereof," filed on May 26, 2017, which applications and their contents are incorporated herein in their entirety by reference.

BACKGROUND OF THE DISCLOSURE

Probiotics—beneficial microorganisms that perform immune modulating functions in humans—have been used both topically and consumed internally to promote general health and aid in healing. Numerous studies have demonstrated the effectiveness of probiotics in promoting human health by aiding in metabolic functions, destroying microorganisms that are harmful to human health, and preventing the colonies of bad microorganisms from developing into problematic diseases or infections. Probiotics must be alive to perform these activities that promote human health.

Probiotics occur naturally, but they are frequently depleted through repeated washing, infections of bad microorganisms, and weakened immune systems. It can take days or even weeks for probiotics to redevelop naturally. During this time, bad microorganisms may proliferate unchecked and cause a variety of health problems. Thus, it is beneficial and desirable to replenish depleted probiotics with live probiotic cultures.

However, delivering live probiotic cultures commercially presents challenges. Live probiotic cultures are comprised of numerous different species of microorganisms that compete with each other for resources. Probiotics generally multiply uncontrollably and unpredictably. Thus, products with live probiotic cultures have short shelf-lives and must be kept refrigerated to ensure that the desired microorganism species are delivered in the desired proportions and quantities.

There are many products on the market that purport to deliver probiotic, but few deliver live probiotic cultures, and none deliver live probiotic cultures and remain shelf-stable over a period of months without refrigeration. There remains a need for a composition capable of delivering controlled quantities and proportions of probiotics that remains shelf-stable over a long period of time without the need for refrigeration.

SUMMARY OF THE INVENTION

The present invention provides stabilized compositions for the controlled delivery of probiotics and methods of producing such compositions. Specifically, the stabilized compositions of the present invention incorporate microencapsulated probiotic beads into a stable hydrogel matrix that release probiotics upon contact with any tissue. The stabilized composition of the present invention allows for a desired combination of various probiotics to remain alive in the quantities and proportions desired. Thus, the present invention allows the controlled delivery of probiotics tailored for specific applications.

In one embodiment of the present invention a stabilized composition for the controlled delivery of probiotics may include an aqueous solution of crystalloids having an osmolality between about 150 mOsm/L and about 500 mOsm/L, wherein the aqueous solution comprises between about 55% to about 95% of the composition by weight. The composition may further include a colloid comprised of water insoluble polymers with the ability to de-swell upon electrical charge, wherein the colloid comprises between about 0.01% to about 1% of the composition by weight. The composition may further include a plurality of oil droplets, wherein the plurality of oil droplets comprise between about 1% to about 50% of the composition by weight. The composition may further include a base solution, wherein the base solution comprises between about 0.01% to about 1% of the composition by weight. The composition may further include a destabilizing solution with an osmolality between 190 mOsm/L and about 900 mOsm/L comprising a solvent, about 0.05% to about 2% nitrogen by weight, a natural acid sufficient to produce a pH of about 3.0 to about 4.5, and a sufficient amount of a salt to contribute to an osmolality between about 190 mOsm/L and about 900 mOsm/L. The composition may further include a plurality of microencapsulated probiotic beads, wherein the plurality of microencapsulated probiotic beads comprises between about 0.01% to about 10% of the composition by weight.

In another embodiment of the present invention, a method of producing a stabilized composition for the controlled delivery of probiotics may include mixing an aqueous solution of crystalloids having an osmolality between 150 mOsm/L and about 900 mOsm/L with a colloid comprised of water insoluble polymers with the ability to de-swell upon electrical charge to form a hydrogel mixture, wherein the aqueous solution comprises between about 55% to about 95% of the composition by weight and the colloid comprises between about 0.01% to about 1% of the composition by weight. The method may further include adding a plurality of oil droplets to the hydrogel mixture, wherein the plurality of oil droplets comprise between about 1% to about 50% of the composition by weight. The method may further include adjusting the pH of the hydrogel mixture to about 6.2 to about 7.2 by adding a base solution, wherein adjusting the pH of the hydrogel mixture causes the lipophilic portions of the water insoluble polymers to surround the plurality of oil droplets, creating a stable gel matrix interspersed with a plurality of oil droplets, and wherein the base solution comprises between about 0.01% to about 1% of the composition by weight. The method may further include partially destabilizing the gel matrix by adding a destabilizing solution with an osmolality between 190 mOsm/L and about 900 mOsm/L comprising a solvent, about 0.05% to about 2% nitrogen by weight, a natural acid sufficient to produce a pH of about 3.0 to about 4.5, and a sufficient amount of a salt to contribute to an osmolality between about 190 mOsm/L and about 900 mOsm/L, wherein adding a concentrated salt solution causes some of the lipophilic portions of the water insoluble polymers to detach from the oil droplets. The method may further include adding a plurality of microencapsulated probiotic beads to the hydrogel mixture, wherein the microencapsulated probiotic beads bind to the detached lipophilic portions of the water insoluble polymers, and wherein the microencapsulated probiotic beads comprises between about 0.01% to about 20% of the composition by weight.

In another embodiment of the present invention, a stabilized composition for the controlled delivery of probiotics is provided, wherein the composition is produced by a method that may include mixing an aqueous solution of crystalloids having an osmolality between 150 mOsm/L and about 500 mOsm/L with a colloid comprised of water insoluble polymers with the ability to de-swell upon electrical charge to form a hydrogel mixture, wherein the aqueous solution comprises between about 55% to about 95% of the composition by weight and the colloid comprises between about 0.01% to about 1% of the composition by weight. The method may further include adding a plurality of oil droplets to the hydrogel mixture, wherein the plurality of oil droplets comprise between about 1% to about 50% of the composition by weight. The method may further include adjusting the pH of the hydrogel mixture to about 6.2 to about 7.2 by adding a base solution, wherein adjusting the pH of the hydrogel mixture causes the lipophilic portions of the water insoluble polymers to surround the plurality of oil droplets, creating a stable gel matrix interspersed with a plurality of oil droplets, and wherein the base solution comprises between about 0.01% to about 1% of the composition by weight. The method may further include partially destabilizing the gel matrix by adding a destabilizing solution with an osmolality between 190 mOsm/L and about 900 mOsm/L comprising a solvent, about 0.05% to about 2% nitrogen by weight, a natural acid sufficient to produce a pH of about 3.0 to about 4.5, and a sufficient amount of a salt to contribute to an osmolality between about 190 mOsm/L and about 900 mOsm/L, wherein adding a concentrated salt solution causes some of the lipophilic portions of the water insoluble polymers to detach from the oil droplets. The method may further include adding a plurality of microencapsulated probiotic beads to the hydrogel mixture, wherein the microencapsulated probiotic beads bind to the detached lipophilic portions of the water insoluble polymers, and wherein the microencapsulated probiotic beads comprises between about 0.01% to about 10% of the composition by weight.

In yet another embodiment of the present invention, the crystalloids are mineral salts, bicarbonates, or other water soluble elements and molecules.

In yet another embodiment of the present invention, the water insoluble polymers are organic polymers.

In yet another embodiment of the present invention, the water insoluble polymers are synthetic polymers.

In yet another embodiment of the present invention, the plurality of oil droplets are comprised of one or more oils selected from the group consisting of plant-based oils, natural fruit-based oils, silicones, dimethicones, esters, essential oils, and eicosene.

In yet another embodiment of the present invention, the base solution is selected from the group consisting of aqueous sodium hydroxide, aqueous sodium citrate, or aqueous triethanolamine (TEA).

In yet another embodiment of the present invention, the composition further comprises a cosmetic preservative.

DETAILED DESCRIPTION

Figure 1:
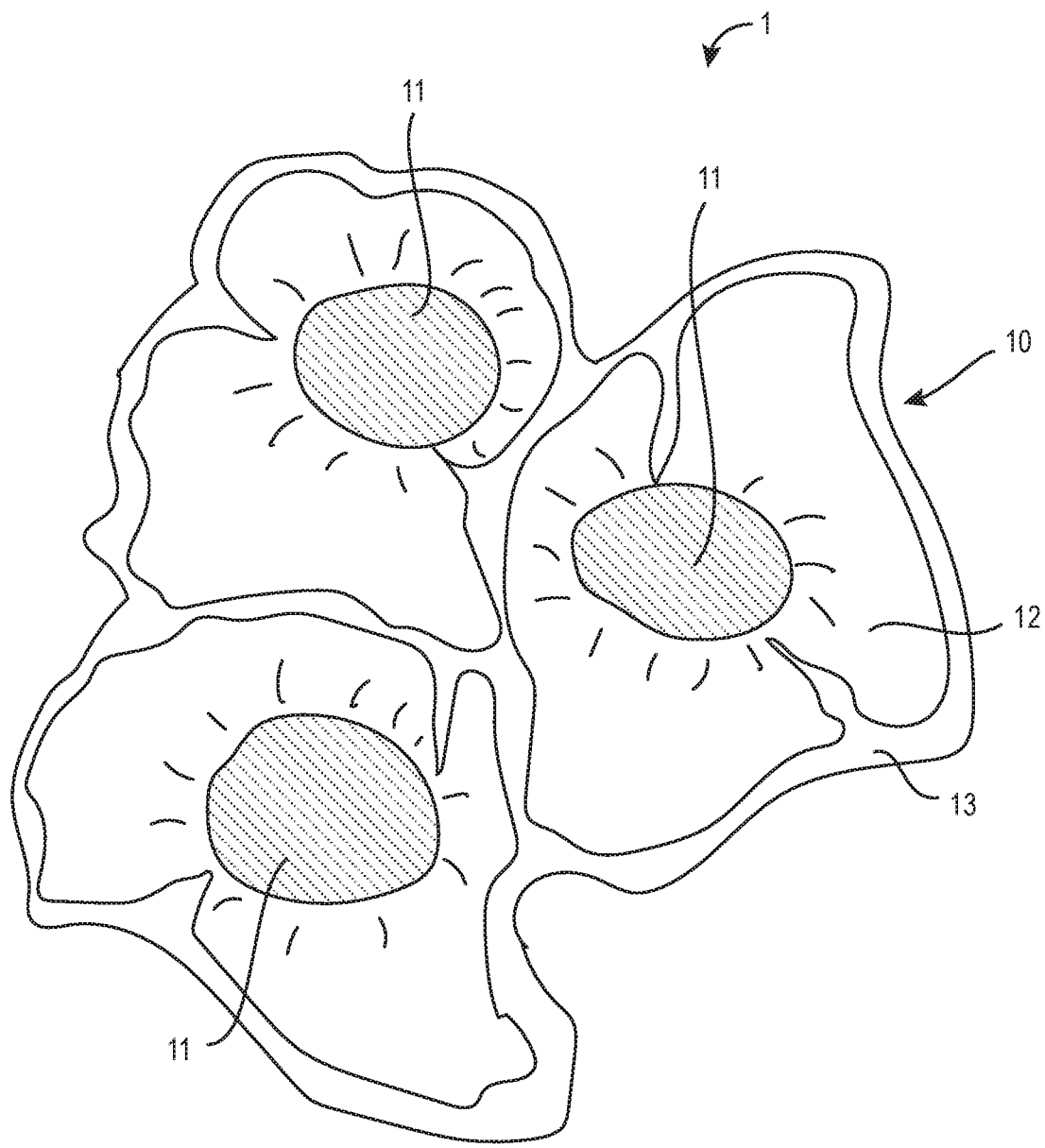
FIG. 1 shows a stable emulsion of oil droplets and a gel matrix according to an embodiment of the present invention.

The presently disclosed subject matter is presented with sufficient details to provide an understanding of one or more particular embodiments of broader inventive subject matters. The descriptions expound upon and exemplify particular features of those particular embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example reference to "an additive" can include a plurality of such additives, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments, +/−10%, in some embodiments +/−5%, in some embodiments +/−1%, in some embodiments +/−0.5%, and in some embodiments, +/−0.1%, from the specified amount, as such variations are appropriate in the disclosed products and methods.

The presently disclosed subject matter provides a stable composition for the controlled delivery of probiotics and methods of production thereof. Advantageously, the present invention provides a composition that can maintain live probiotic cultures in desired quantities and proportions over long periods of time without the need for refrigeration, allowing for the delivery of live probiotic cultures in a variety of shelf-stable products.

According to some embodiments of the present invention, a stabilized composition for the controlled delivery of probiotics may comprise an aqueous solution of crystalloids having an osmolality between about 150 mOsm/L and about 500 mOsm/L, wherein the aqueous solution comprises between about 55% to about 95% of the composition by weight. The composition may further comprise a colloid comprised of water insoluble polymers with the ability to de-swell upon electrical charge, wherein the colloid comprises between about 0.01% to about 1% of the composition by weight. The composition may further comprise a plurality of oil droplets, wherein the plurality of oil droplets comprise between about 1% to about 50% of the composition by weight. The composition may further comprise a base solution, wherein the base solution comprises between about 0.01% to about 1% of the composition by weight. a destabilizing solution with an osmolality between 190 mOsm/L and about 900 mOsm/L comprising a solvent, about 0.05% to about 2% nitrogen by weight, a natural acid sufficient to produce a pH of about 3.0 to about 4.5, and a sufficient amount of a salt to contribute to an osmolality between about 190 mOsm/L and about 900 mOsm/L. The composition may further comprise a plurality of microencapsulated probiotic beads, wherein the plurality of microencapsulated probiotic beads comprises between about 0.01% to about 20% of the composition by weight.

The composition of the present invention comprises four primary phases. The aqueous phase is an aqueous solution of crystalloids. The crystalloids may be any water soluble molecules. Preferably, the crystalloids are mineral salts, bicarbonates, glucose or other simple sugars, antibodies, albumin, other proteins that mimic human plasma, or other water soluble elements. Examples of such crystalloids include, but are not limited to potassium, sodium, chlorine, magnesium, calcium, zinc, copper, selenium, oxygen, etc. The specific combination of crystalloids used in the present invention may be water soluble elements and molecules sufficient to promote the growth of the desired probiotic blend. The aqueous phase may preferably contain a sufficient concentration of crystalloids to achieve an osmolality similar to that of human plasma, or of about 250 mOsm/L to about 350 mOsm/L, but may have an osmolality significantly less than or greater than 250 mOsm/L to about 350 mOsm/L depending on the specific application.

The aqueous phase may further include a base solution and a destabilizing solution, which are described in further details below.

etc. and other commercially available synthetic polymers may also be used in the present invention.

The oil phase of the present invention may comprise any polar and non-polar oils, plant-based oils, natural fruit-based oils, esters, isododecane, essential oils, synethetic oils, dimethicone, silicone, PVP/eicosene copolymers and other similar oils. The oil phase may comprise between about 1% to about 50% of the composition by weight, depending on the specific application of the product.

The microencapsulated probiotic beads comprise microcapsules possessing Lewis-acid Lewis-base salt walls incorporating water-immiscible materials enclosing dormant probiotics. Preferably, the water-immiscible materials are oils or other lipophilic materials, making the microencapsulated probiotic beads attractive to lipophilic molecules. The production of such microcapsules are well-known in the art. For example, U.S. Pat. No. 8,685,425 to Speaker discloses exemplary methods of producing said microcapsules. The microencapsulated probiotic beads of the present invention may deliver any desired combination of probiotics from about 50 colony forming units per gram to about 1,000,000 and/or to TNTC (too numerous to count) colony forming units per gram as required by the specifically contemplated application. Table 1 shows the number of probiotic colony forming units per gram delivered based on the percentage of microencapsulated probiotic of the total composition by weight in an exemplary formulation of the present invention.

TABLE 1

CONTROLLED PROBIOTIC DELIVERY TABLE

| Formula # | FN1-RT0-190 (Control) | FN1-200 (a) | FN1-200 (b) | FN1-200 (c) | FN1-200 (d) | FN1-200 (e) |
|---|---|---|---|---|---|---|
| % of microencapsulated probiotic of total composition by weight | 0.0% | 20.0% | 0.06% | 3.0% | 0.3% | 2.0% |
| Total Bacteria Count (colony forming units/gram) | None Detected | TNTC | 210 cfu/g | $2.25 \times 10^4$ cfu/g | $265 \times 10^4$ cfu/g | $1.44 \times 10^4$ cfu/g |

The colloid phase of the composition comprises large water insoluble molecules polymers. Polymers suitable for use in the present invention should have an effective use level of between about 0.01% to about 1% to create a gel matrix, and de-swell upon contact with an electrical-charge. Said polymers may be of natural origin; for example, cellulose, plant or animal based gelatin, or collagen may be used as colloids. Synthetic polymers including, but not limited to acrylates, carbomers, PVP/eicosene copolymers, In the compositions of the present invention, the colloids form a gel matrix within the aqueous phase. Oil droplets and microencapsulated probiotic beads are interspersed within the matrix, "anchored" at lipophilic portions of the colloids throughout the matrix. The process of creating such a configuration of the four primary phases is discussed in further detail below. In such a configuration, the microencapsulated probiotic beads remain protected and stable over a period of 18 months at temperatures as high as 40 degrees Celsius, as shown in Table 2.

TABLE 2

18-MONTH STABILITY TABLE

| Test Description | 0 Months | 3 Months | 6 Months | 12 Months | 18 Months |
|---|---|---|---|---|---|
| pH | 5.8 | 6.1 | 6.0 | 5.9 | 5.9 |
| Probiotic Aerobic Plate Count (cfu/ml) | $6.9 \times 10^5$ cfu/g | $5.9 \times 10^5$ cfu/g | N/A | $5.3 \times 10^5$ cfu/g | $2.61 \times 10^4$ cfu/g |
| Mold/Yeast Count (cfu/ml) | Non-detectable | Non-detectable | Non-detectable | Non-detectable | Non-detectable |
| Undesirable Biotics | Non-detectable | Non-detectable | Non-detectable | Non-detectable | Non-detectable |

A cosmetic preservative may be added to the final composition to aid in shelf-stability.

According to some embodiments of the present invention, a method of producing a stabilized composition for the controlled delivery of probiotics may comprise mixing an aqueous solution of crystalloids having an osmolality between 150 mOsm/L and about 500 mOsm/L with a colloid comprised of water insoluble polymers with the ability to de-swell upon electrical charge to form a hydrogel mixture, wherein the aqueous solution comprises between about 55% to about 95% of the composition by weight and the colloid comprises between about 0.01% to about 1% of the composition by weight. The method may further comprise adding a plurality of oil droplets to the hydrogel mixture, wherein the plurality of oil droplets comprise between about 1% to about 50% of the composition by weight. The method may further comprise adjusting the pH of the hydrogel mixture to about 6.2 to about 7.2 by adding a base solution, wherein adjusting the pH of the hydrogel mixture causes the lipophilic portions of the water insoluble polymers to surround the plurality of oil droplets, creating a stable gel matrix interspersed with a plurality of oil droplets, and wherein the base solution comprises between about 0.01% to about 1% of the composition by weight. The method may further comprise partially destabilizing the gel matrix by adding a destabilizing solution with an osmolality between 190 mOsm/L and about 900 mOsm/L comprising a solvent, about 0.05% to about 2% nitrogen by weight, a natural acid sufficient to produce a pH of about 3.0 to about 4.5, and a sufficient amount of a salt to contribute to an osmolality between about 190 mOsm/L and about 900 mOsm/L, wherein adding a concentrated salt solution causes some of the lipophilic portions of the water insoluble polymers to detach from the oil droplets. The method may further comprise adding a plurality of microencapsulated probiotic beads to the hydrogel mixture, wherein the microencapsulated probiotic beads bind to the detached lipophilic portions of the water insoluble polymers, and wherein the microencapsulated probiotic beads comprises between about 0.01% to about 20% of the composition by weight.

Referring now to FIG. 1, a stable emulsion 1 of a gel matrix 10 and oil droplets 11 is shown. The aqueous solution 12 and colloids 13 are mixed to from a hydrogel mixture. Once oil droplets 11 are added to the hydrogel mixture, the oil droplets 11 are attracted to the lipophilic portions of the colloids 13, preventing the oil droplets 11 from aggregating into larger pools of oil. Once the pH of the hydrogel mixture is increased to between about 6.2 to about 7.2 by adding a base solution, the colloids 13 form a matrix 10 dispersed within the water phase, with oil droplets 11 interspersed within the matrix 10 "anchored" to lipophilic portions of the colloids 13. Thus, the stable emulsion 1 of a gel matrix 10 and oil droplets 11 as shown in FIG. 1 is formed. The base solution used to neutralize the hydrogel mixture may be comprised of any base or alkaline pH adjusters, but is preferably sodium hydroxide, sodium citrate, or triethanolamine (TEA) in exemplary embodiments.

Figure 2:
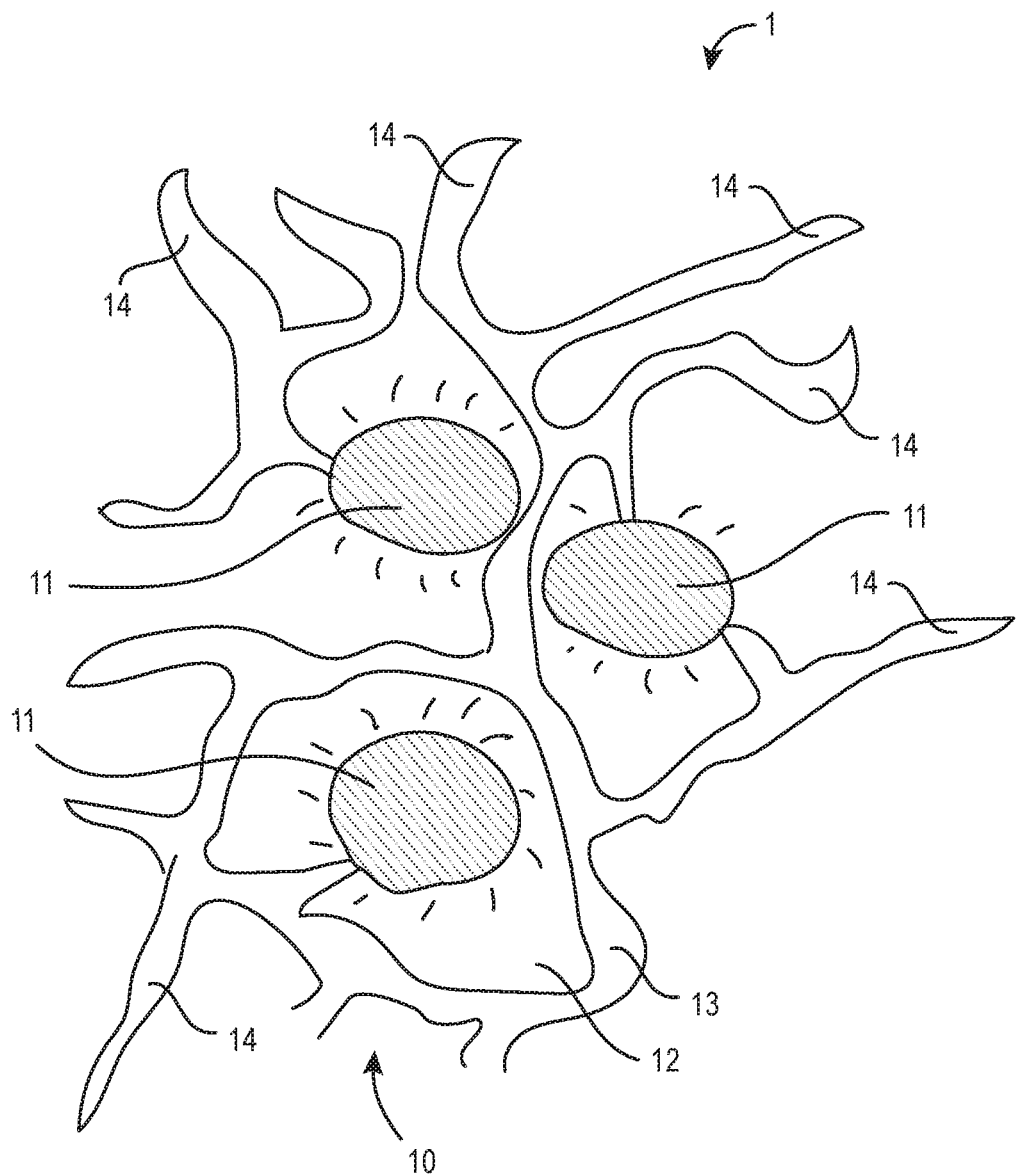
FIG. 2 shows a partially destabilized emulsion of oil droplets and a gel matrix according to an embodiment of the present invention.

Referring now to FIG. 2, the stable emulsion 1 of a gel matrix 10 and oil droplets 11 is partially destabilized to create free lipophilic "anchor" sites 14 for the microencapsulated probiotic beads 15 (not shown in FIG. 2). Destabilization is achieved by adding a destabilizing solution to the emulsion. Suitable destabilizing solutions may comprise a solvent, preferably water. Said solutions may further comprise about 0.05% to about 2% nitrogen of the solution by weight, a sufficient amount of a natural source of acid to produce a pH of about 3.0 to about 4.5 in the destabilizing solution, and a sufficient amount of a salt to contribute to an osmolality between about 190 mOsm/L and about 900 mOsm/L in the destabilizing solution. The salt may be any salt, but is preferably sodium chloride in exemplary embodiments.

Figure 3:
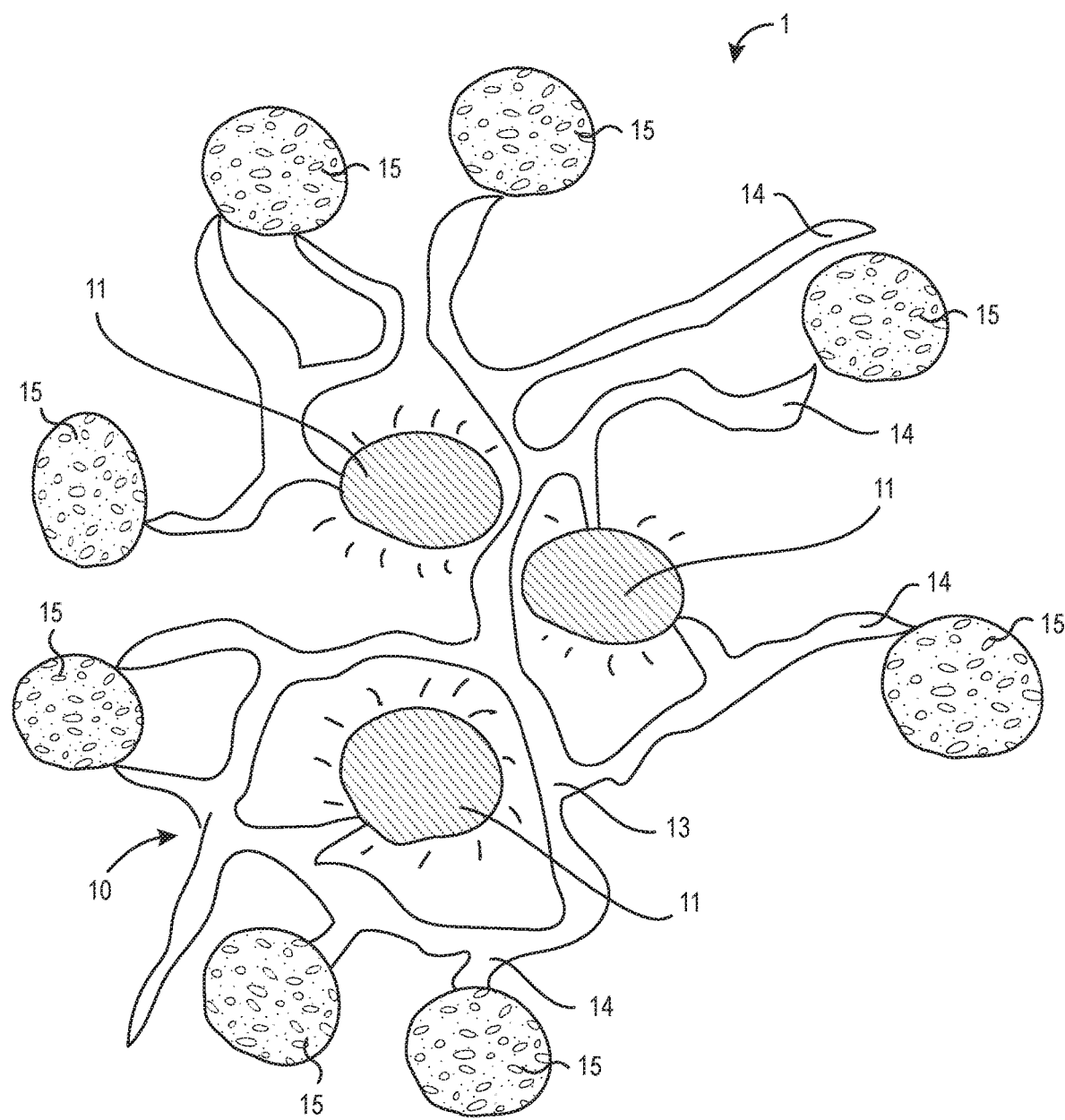
FIG. 3 shows a stable emulsion of microencapsulated probiotics according to an embodiment of the present invention.

Referring now to FIG. 3, microencapsulated probiotic beads 15 comprising between about 0.01% to about 20% of the composition by weight are added to the destabilized emulsion. The microencapsulated probiotic beads 15 will bind to the open lipophilic anchor sites 14 of the colloids 13, once again forming a stabilized emulsion of gel matrix 10, oil droplets 11, and microencapsulated probiotic beads 15. As shown in Table 1, the amount of probiotics delivered can be controlled by varying the amount of microencapsulated probiotic beads 15 incorporated into the composition.

The following examples relate to the production and the composition of the stabilized compositions for the controlled delivery of probiotics according to embodiments of the present invention. All percentages provided in the examples are percentage by weight of the total weight of the final composition.

Example 1

Exemplary formulation FN1-200(a) described in Table 1 was produced by (a) combining in a first vessel 42.42% water, polysaccharides, NaCl, minerals, enzymes, and vitamins sufficient to yield and osmolality of 290 mOsm/L; 0.1% phytic acid; 0.1% ascorbic acid; 3.0% glycerin; 0.3% carbomer/polymer;

(b) combining in a second vessel 3.0% octyldodecyl myristate; 3.0% avocado oil; 6.0% jojoba seed oil; 5.0% squalene; 0.98% tocopherol; 5.0% *Cannabis sativa* seed oil; 2.0% bisabolol; 3.0% *Hypericum perforatum* oil; 1.0% *Hippophae rhamnoides* fruit oil and heating the ingredients to about 60 about 70 degrees Celsius;

(c) adding the contents of the second vessel to the contents of the first vessel while mixing with sufficient sheer force to create a stable emulsion;

(d) allowing the stable emulsion to cool to about 30 degrees Celsius;

(e) adjusting the pH of the stable emulsion by adding 0.6% sodium hydroxide;

(f) destabilizing the mixture with 3.5% saline with an osmolality of 290 mOsm/L;

(g) adding 3.0% probiotic microbeads;

(h) adding 1.0% cosmetic preservative.

Example 2

Exemplary formulation FN1-200(b) described in Table 1 was produced by (a) combining in a first vessel 62.36% water, polysaccharides, NaCl, minerals, enzymes, and vitamins sufficient to yield and osmolality of 290 mOsm/L; 0.1% phytic acid; 0.1% ascorbic acid; 3.0% glycerin; 0.3% carbomer/polymer;

(b) combining in a second vessel 3.0% octyldodecyl myristate; 3.0% avocado oil; 6.0% jojoba seed oil; 5.0% squalene; 0.98% tocopherol; 5.0% *Cannabis sativa* seed oil; 2.0% bisabolol; 3.0% *Hypericum perforatum* oil; 1.0% *Hippophae rhamnoides* fruit oil and heating the ingredients to about 60 about 70 degrees Celsius;

(c) adding the contents of the second vessel to the contents of the first vessel while mixing with sufficient sheer force to create a stable emulsion;

(d) allowing the stable emulsion to cool to about 30 degrees Celsius;

(e) adjusting the pH of the stable emulsion by adding 0.6% sodium hydroxide;
(f) destabilizing the mixture with 3.5% saline with an osmolality of 290 mOsm/L;
(g) adding 0.6% probiotic microbeads;
(h) adding 1.0% cosmetic preservative.

Example 3

Exemplary formulation FN1-200(c) described in Table 1 was produced by
(a) combining in a first vessel 59.42% water, polysaccharides, NaCl, minerals, enzymes, and vitamins sufficient to yield and osmolality of 290 mOsm/L; 0.1% phytic acid; 0.1% ascorbic acid; 3.0% glycerin; 0.3% carbomer/polymer;
(b) combining in a second vessel 3.0% octyldodecyl myristate; 3.0% avocado oil; 6.0% jojoba seed oil; 5.0% squalene; 0.98% tocopherol; 5.0% *Cannabis sativa* seed oil; 2.0% bisabolol; 3.0% *Hypericum perforatum* oil; 1.0% *Hippophae rhamnoides* fruit oil and heating the ingredients to about 60 about 70 degrees Celsius;
(c) adding the contents of the second vessel to the contents of the first vessel while mixing with sufficient sheer force to create a stable emulsion;
(d) allowing the stable emulsion to cool to about 30 degrees Celsius;
(e) adjusting the pH of the stable emulsion by adding 0.6% sodium hydroxide;
(f) destabilizing the mixture with 3.5% saline with an osmolality of 290 mOsm/L;
(g) adding 3.0% probiotic microbeads;
(h) adding 1.0% cosmetic preservative.

Example 4

Exemplary formulation FN1-200(d) described in Table 1 was produced by
(a) combining in a first vessel 62.12% water, polysaccharides, NaCl, minerals, enzymes, and vitamins sufficient to yield and osmolality of 290 mOsm/L; 0.1% phytic acid; 0.1% ascorbic acid; 3.0% glycerin; 0.3% carbomer/polymer;
(b) combining in a second vessel 3.0% octyldodecyl myristate; 3.0% avocado oil; 6.0% jojoba seed oil; 5.0% squalene; 0.98% tocopherol; 5.0% *Cannabis sativa* seed oil; 2.0% bisabolol; 3.0% *Hypericum perforatum* oil; 1.0% *Hippophae rhamnoides* fruit oil and heating the ingredients to about 60 about 70 degrees Celsius;
(c) adding the contents of the second vessel to the contents of the first vessel while mixing with sufficient sheer force to create a stable emulsion;
(d) allowing the stable emulsion to cool to about 30 degrees Celsius;
(e) adjusting the pH of the stable emulsion by adding 0.6% sodium hydroxide;
(f) destabilizing the mixture with 3.5% saline with an osmolality of 290 mOsm/L;
(g) adding 0.3% probiotic microbeads;
(h) adding 1.0% cosmetic preservative.

Example 5

Exemplary formulation FN1-200(e) described in Table 1 was produced by
(a) combining in a first vessel 60.42% water, polysaccharides, NaCl, minerals, enzymes, and vitamins sufficient to yield and osmolality of 290 mOsm/L; 0.1% phytic acid; 0.1% ascorbic acid; 3.0% glycerin; 0.3% carbomer/polymer;
(b) combining in a second vessel 3.0% octyldodecyl myristate; 3.0% avocado oil; 6.0% jojoba seed oil; 5.0% squalene; 0.98% tocopherol; 5.0% *Cannabis sativa* seed oil; 2.0% bisabolol; 3.0% *Hypericum perforatum* oil; 1.0% *Hippophae rhamnoides* fruit oil and heating the ingredients to about 60 about 70 degrees Celsius;
(c) adding the contents of the second vessel to the contents of the first vessel while mixing with sufficient sheer force to create a stable emulsion;
(d) allowing the stable emulsion to cool to about 30 degrees Celsius;
(e) adjusting the pH of the stable emulsion by adding 0.6% sodium hydroxide;
(f) destabilizing the mixture with 3.5% saline with an osmolality of 290 mOsm/L;
(g) adding 2.0% probiotic microbeads;
(h) adding 1.0% cosmetic preservative.

Example 6

Exemplary formulation FN1-126 described in Table 2 was produced by
(a) combining in a first vessel 60.42% water, polysaccharides, NaCl, minerals, enzymes, and vitamins sufficient to yield and osmolality of 320 mOsm/L; 0.5% ascorbic acid; 3.0% glycerin; 0.3% carbomer/polymer; 0.02% sodium phytate;
(b) combining in a second vessel 3.0% octyldodecyl myristate; 1.0% avocado oil; 2.0% jojoba seed oil; 3.0% squalene; 0.98% tocopherol; 2.0% *Cannabis sativa* seed oil; 2.0% bisabolol; 3.0% *Hypericum perforatum* oil; 3.0% *Hippophae rhamnoides* fruit oil and heating the ingredients to about 60 about 70 degrees Celsius;
(c) adding the contents of the second vessel to the contents of the first vessel while mixing with sufficient sheer force to create a stable emulsion;
(d) allowing the stable emulsion to cool to about 30 degrees Celsius;
(e) adjusting the pH of the stable emulsion by adding 0.6% sodium hydroxide;
(f) destabilizing the mixture with 4.5% saline with an osmolality of 320 mOsm/L;
(g) adding 3.0% probiotic microbeads;
(h) adding 1.0% cosmetic preservative.

Example 7

Another exemplary formulation according to an embodiment of the present invention is produced by
(a) combining in a first vessel 59.42% water, polysaccharides, NaCl, minerals, enzymes, and vitamins sufficient to yield and osmolality of 700 mOsm/L; 0.1% phytic acid; 0.1% ascorbic acid; 3.0% butylene glycol; 0.3% carbomer/polymer;
(b) combining in a second vessel 3.0% capryliccapric triglycerides; 3.0% avocado oil; 6.0% jojoba seed oil; 5.0% squalene; 0.98% tocopherol; 5.0% *Cannabis sativa* seed oil; 2.0% bisabolol; 3.0% *Hypericum perforatum* oil; 1.0% *Hippophae rhamnoides* fruit oil and heating the ingredients to about 60 about 70 degrees Celsius;
(c) adding the contents of the second vessel to the contents of the first vessel while mixing with sufficient sheer force to create a stable emulsion;
(d) allowing the stable emulsion to cool to about 30 degrees Celsius;

(e) adjusting the pH of the stable emulsion by adding 0.6% sodium hydroxide;

(f) destabilizing the mixture with 3.5% saline with an osmolality of 290 mOsm/L;

(g) adding 3.0% probiotic microbeads;

(h) adding 1.0% cosmetic preservative.

Example 8

Another exemplary formulation according to an embodiment of the present invention is produced by (a) combining in a first vessel 59.42% water, aloe juice, polysaccharides, NaCl, minerals, enzymes, and vitamins sufficient to yield and osmolality of 260 mOsm/L; 0.1% phytic acid; 0.1% ascorbic acid; 3.0% ethylhexylglycerin; 0.3% carbomer/polymer;

(b) combining in a second vessel 3.0% ester mixture of dicaprylyl maleate and ethylhexyl palmitate; 3.0% avocado oil; 6.0% jojoba seed oil; 5.0% squalene; 0.98% tocopherol; 5.0% *Cannabis sativa* seed oil; 2.0% bisabolol; 3.0% *Hypericum perforatum* oil; 1.0% hippophae rhamnoides fruit oil and heating the ingredients to about 60 about 70 degrees Celsius;

(c) adding the contents of the second vessel to the contents of the first vessel while mixing with sufficient sheer force to create a stable emulsion;

(d) allowing the stable emulsion to cool to about 30 degrees Celsius;

(e) adjusting the pH of the stable emulsion by adding 0.6% sodium hydroxide;

(f) destabilizing the mixture with 3.5% saline with an osmolality of 290 mOsm/L;

(g) adding 3.0% probiotic microbeads;

(h) adding 1.0% cosmetic preservative.

Example 9

Another exemplary formulation according to an embodiment of the present invention is produced by (a) combining in a first vessel 59.42% water, polysaccharides, NaCl, minerals, enzymes, and vitamins sufficient to yield and osmolality of 190 mOsm/L; 0.2% citric acid; 3.0% propendoil; 0.3% carbomer/polymer;

(b) combining in a second vessel 3.0% C10-18 triglycerides; 3.0% avocado oil; 6.0% jojoba seed oil; 5.0% squalene; 0.98% tocopherol; 5.0% *Cannabis sativa* seed oil; 2.0% bisabolol; 3.0% *Hypericum perforatum* oil; 1.0% *Hippophae rhamnoides* fruit oil and heating the ingredients to about 60 about 70 degrees Celsius;

(c) adding the contents of the second vessel to the contents of the first vessel while mixing with sufficient sheer force to create a stable emulsion;

(d) allowing the stable emulsion to cool to about 30 degrees Celsius;

(e) adjusting the pH of the stable emulsion by adding 0.6% sodium hydroxide;

(f) destabilizing the mixture with 3.5% saline with an osmolality of 190 mOsm/L;

(g) adding 3.0% probiotic microbeads;

(h) adding 1.0% cosmetic preservative.

Those skilled in the art will recognize improvements and modifications to the embodiments of the present disclosure. All such improvements and modifications are considered within the scope of the concepts disclosed herein and the claims that follow.

What is claimed:

1. A stabilized composition for the controlled delivery of probiotics comprising:

an aqueous solution of crystalloids comprising one or more of: aloe juice, polysaccharides, NaCl, minerals, enzymes and vitamins, wherein the crystalloids have an osmolality between about 150 mOsm/L and about 900 mOsm/L, and wherein the aqueous solution comprises between about 55% to about 95% of the composition by weight;

a colloid comprised of water insoluble polymers comprising carbomers, wherein the polymers have the ability to de-swell upon electrical charge, and wherein the colloid comprises between about 0.01% to about 1% of the composition by weight;

a plurality of charged oil droplets comprising one or more of: C10-18 triglycerides, ester mixture of dicaprylyl maleate and ethylhexyl palmitate, octyldodecyl myristate, avocado oil, jojoba seed oil, squalene, tocopherol, *Cannabis sativa* seed oil, bisabolol, *Hypericum perforatum* oil, and *Hippophae rhamnoides* fruit oil, wherein the plurality of charged droplets comprise between about 1% to about 50% of the composition by weight;

a base solution comprising aqueous sodium hydroxide, wherein the base solution comprises between about 0.01% to about 1% of the composition by weight;

a destabilizing solution with an osmolality between 190 mOsm/L and about 900 mOsm/L comprising:

a solvent;

about 0.05% to about 2% nitrogen by weight;

an acid comprising one or more of: phytic acid, ascorbic acid and citric acid, an amount of the acid sufficient to produce a pH of about 3.0 to about 4.5;

an amount of a salt capable of contributing to an osmolality between about 190 mOsm/L and about 900 mOsm/L; and a plurality of microencapsulated probiotic beads, wherein the plurality of microencapsulated probiotic beads comprises between about 0.01% to about 20% of the composition by weight.

2. The composition of claim 1 further comprising a cosmetic preservative.

3. A stabilized composition for the controlled delivery of probiotics, wherein the composition is produced by a method comprising:

mixing an aqueous solution of crystalloids having an osmolality between 150 mOsm/L and about 500 mOsm/L with a colloid comprised of water insoluble polymers with the ability to de-swell upon electrical charge to form a hydrogel mixture, wherein the crystalloids comprise one or more of: aloe juice, polysaccharides, NaCl, minerals, enzymes and vitamins;

wherein the water insoluble polymers comprise carbomers;

wherein the aqueous solution comprises between about 55% to about 95% of the composition by weight and the colloid comprises between about 0.01% to about 1% of the composition by weight;

adding a plurality of charged oil droplets to the hydrogel mixture, wherein the plurality of charged oil droplets comprise one or more of: C10-18 triglycerides, ester mixture of dicaprylyl maleate and ethylhexyl palmitate, octyldodecyl myristate, avocado oil, jojoba seed oil, squalene, tocopherol, *Cannabis sativa* seed oil, bisabolol, *Hypericum perforatum* oil, and *Hippophae*

*rhamnoides* fruit oil, wherein the plurality of charged droplets comprise between about 1% to about 50% of the composition by weight;

adjusting the pH of the hydrogel mixture to about 6.2 to about 7.2 by adding a base solution comprising aqueous sodium hydroxide,
- wherein adjusting the pH of the hydrogel mixture causes the lipophilic portions of the water insoluble polymers to surround the plurality of oil droplets, creating a stable gel matrix interspersed with a plurality of oil droplets, and
- wherein the base solution comprises between about 0.01% to about 1% of the composition by weight;

destabilizing the gel matrix by adding a destabilizing solution with an osmolality between 190 mOsm/L and about 900 mOsm/L comprising:
- a solvent;
- about 0.05% to about 2% nitrogen by weight;
- an acid comprising one or more of: phytic acid, ascorbic acid and citric acid, an amount of the acid sufficient to produce a pH of about 3.0 to about 4.5;
- an amount of a salt capable of contributing to an osmolality between about 190 mOsm/L and about 900 mOsm/L;
- wherein adding the destabilizing solution causes some of the lipophilic portions of the water insoluble polymers to detach from the charged oil droplets;

adding a plurality of microencapsulated probiotic beads to the hydrogel mixture,
- wherein the microencapsulated probiotic beads bind to the detached lipophilic portions of the water insoluble polymers, and
- wherein the microencapsulated probiotic beads comprises between about 0.01% to about 20% of the composition by weight.

4. The composition of claim 3 produced by a method further comprising adding about 1.0% of the composition by weight cosmetic preservative.

* * * * *